US005647051A

United States Patent [19]
Neer

[11] Patent Number: 5,647,051
[45] Date of Patent: Jul. 8, 1997

[54] COLD THERAPY SYSTEM WITH INTERMITTENT FLUID PUMPING FOR TEMPERATURE CONTROL

[75] Inventor: Charles S. Neer, Milford, Ohio

[73] Assignee: Seabrook Medical Systems, Inc., Cincinnati, Ohio

[21] Appl. No.: 392,036

[22] Filed: Feb. 22, 1995

[51] Int. Cl.$^6$ ........................................ H02P 5/17
[52] U.S. Cl. ........................................ 388/811; 607/104
[58] Field of Search ........................................ 388/811, 809, 388/812–815; 607/96, 104, 108–111; 146/46

[56] References Cited

U.S. PATENT DOCUMENTS

| | | |
|---|---|---|
| 1,896,953 | 2/1933 | Hassell . |
| 2,726,658 | 12/1955 | Chessey . |
| 3,918,458 | 11/1975 | Nethery . |
| 4,112,943 | 9/1978 | Adams . |
| 4,459,468 | 7/1984 | Bailey . |
| 4,821,354 | 4/1989 | Little . |
| 4,960,103 | 10/1990 | Urso . |
| 5,174,285 | 12/1992 | Fontenot . |
| 5,183,039 | 2/1993 | Sarian et al. . |
| 5,241,951 | 9/1993 | Mason et al. . |
| 5,241,958 | 9/1993 | Noeldner . |
| 5,330,519 | 7/1994 | Mason et al. . |
| 5,388,176 | 2/1995 | Dykstra et al. ........................ 388/811 |

OTHER PUBLICATIONS

Sales Brochure—Polar Care Cold Therapy Pump, Breg, Inc., 1281 Liberty Way, Vista, CA 92083, 1991.
Sales Brochure—Aircast Cryo–Cuff, Aircast, Incorporated, P.O. Box 709, Summit, New Jersey 07902–0709, 1991.
Sales Brochure—Polar Care Cub, Breg, Inc., 1281 Liberty Way, Vista, CA 92083, 1994.

Primary Examiner—David S. Martin
Attorney, Agent, or Firm—Frost & Jacobs

[57] ABSTRACT

A cold therapy system for applying a cooling pad to an area of the body of the user. The system comprises a portable insulated cooler having a lid and serving as a reservoir for water and ice. A pump is located within a housing affixed to the exterior of the cooler. The pump has an inlet operatively connected to the reservoir through the adjacent cooler wall. The pump has an outlet connected by an insulated delivery tube to the inlet of a pad. The outlet of the pad is connected by an insulated return tube, through the cooler wall to which the pump housing is affixed, to the reservoir. The pump is provided with a pulse-width modulating circuit having an electronic switch output that switches an intermittent drive current to the pump motor according to any one of a number of predetermined operating modes selectable by the operator through the use of a manual switch. Each of the operating modes provides the pad with a predetermined and repeatable temperature by altering the operating duty cycle of the drive current to the motor, the drive current being a combination of a medium fixed frequency pulse train having a fixed duty cycle and a very low fixed frequency DC pulse having a variable pulse width. The intermittent running of the pump motor further results in a compressive massaging effect by the pad.

18 Claims, 7 Drawing Sheets

COLD THERAPY SYSTEM WITH INTERMITTENT FLUID PUMPING FOR TEMPERATURE CONTROL

TECHNICAL FIELD

The invention relates to a cold therapy system of the type wherein cold water is circulated between a body contacting pad and a cooler by a pump and a delivery and return tube assembly, and more particularly to such a system wherein the temperature of the water in the pad is precisely controlled by altering the operating duty cycle of a pulsating drive current for the pump motor, which additionally results in a compressive or massaging effect applied to the user by the pad.

BACKGROUND ART

There are a number of instances, inclusive of injuries, surgery and the like, for which cold therapy is prescribed. To this end, water circulating pads have been devised in various sizes and shapes to be applied against or wrapped about a body part to be treated. Each pad has an inlet and an outlet and a path within the pad extending between the inlet and the outlet. Cold water can thereby be introduced into the pad, circulated through the pad, and removed therefrom.

In recent years there has been a marked increase in sports activities, for example, and a marked increase in a number of people participating therein. As a result, there has been an increased demand for a simple, portable, cold therapy system, capable of use in the home or elsewhere. It will further be understood that the use of such systems is not limited to sports injuries.

Prior art workers have devised a number of cold therapy systems in an attempt to meet this demand. One approach is to provide a pad for application to the body area to be treated, a cooler filled with ice and water, and a tube extending from the cooler to the pad. The cooler is held above the pad so that chilled water is introduced into the pad from the cooler by gravity. As the chilled water in the pad warms from body heat, the cooler can be placed in a position below the pad, causing the pad to drain into the cooler. After a short time the water is recooled by the ice in the cooler and the process may be repeated. Such a system requires considerable manipulation by the user, and does not provide an even, controlled cold temperature at the treatment site.

Recently, a number of prior art workers have devised cold therapy systems wherein cold water is continuously circulated from a reservoir through a pad and back to the reservoir by means of a pump. A number of these systems have means for regulating the temperature of the water passing through the pad. An early approach, for example, was simply to regulate the temperature of the water, itself, within the reservoir. Another approach is described in U.S. Pat. No. 5,241,951. This reference teaches the provision of a reservoir and a pump submersible therein. The outlet of the pump is connected to the inlet of the pad by appropriate conduit means. The outlet of the pad is connected to the reservoir by a suitable return conduit. Temperature regulation is achieved by an in-line valve in the form of an adjustable flow restrictor located in either one of the conduits, but preferably in the return conduit. By closing the valve to reduce the flow rate of the fluid, temperature in the pad increases due to heat transfer. By opening the valve to increase the flow rate, temperature in the pad decreases. Since the flow restrictor valve is in the form of a stop cock valve, precise adjustment and precisely repeatable adjustments are difficult, if not substantially impossible, to make.

U.S. Pat. No. 5,476,489 entitled COLD THERAPY SYSTEM there is taught a system comprising a reservoir incorporating a cooler having insulative walls, an insulative bottom, and an insulative closure lid. A non-submersible pump and a housing therefore are attached to the exterior of one of the cooler walls. The inlet of the pump is connected to the reservoir and the outlet of the pump is connected to a treatment pad through an insulated delivery tube. The pad is connected by an insulated return tube to the reservoir. The insulated return tube may have a liquid crystal temperature indicator located therein. The pump is of a multi-speed design, enabling control of the water temperature within the pad by means of flow rate, eliminating the need for an adjustable flow restricting valve. For reasons made evident hereinafter, the teachings of this co-pending application are herein incorporated by reference. A problem encountered with this approach is poor pump performance at extremely low speeds.

The present invention is directed to a cold therapy system which overcomes a number of these deficiencies of the prior art systems. According to the present invention, a reservoir for water and ice is provided in the form of a standard cooler having a closure lid. The reservoir is connected to a treatment pad through a non-submersible pump and an insulated delivery tube. The pad is connected by an insulated return tube to the reservoir. The pump is mounted in a housing affixed to the exterior of the cooler so that the ice and water are isolated from any heat generated by the pump.

The pump of the present invention is of a single-speed design. As will be described more fully hereinafter, control of the water temperature in the pad is accomplished by running the pump in any one of a number of selectable intermittent modes. In this way the water temperature is more precisely controlled in a repeatable manner. Furthermore, the problems encountered when running a pump at very low speeds are eliminated. The delivery tube is provided with a check valve and the return tube is provided with a flow control orifice or other appropriate restriction means, for reasons set forth hereinafter. Finally, the system may be provided with a temperature indicator located in either the delivery tube or return tube.

DISCLOSURE OF THE INVENTION

According to the invention there is provided a cold therapy system for applying a cooling pad to an area of the body of the user. The system comprises a portable insulated cooler having a lid. The cooler serves as a reservoir for water and ice. A pump is located within a housing affixed to the exterior of the cooler. The pump has an inlet operatively connected to the reservoir of water and ice through the adjacent cooler wall. The pump has an outlet connected by means of an insulated delivery tube to the inlet of a water circulating pad. The outlet of the pad is connected by an insulated return tube, through the cooler wall to which the pump housing is affixed, to the reservoir.

The pump is provided with a pulse-width modulating circuit having an electronic switch output that switches an intermittent drive current to the pump motor according to any one of a number of predetermined operating modes selectable by the operator through the use of a manual switch. Each of the operating modes provides the cold therapy system pad with a predetermined and repeatable temperature by altering the operating duty cycle of the drive current to the motor, the drive current being a combination of a medium fixed frequency pulse train having a fixed duty cycle and a very low fixed frequency DC pulse having a variable pulse width.

A temperature indicator may be located within one of the delivery and return tubes.

The intermittent running of the pump motor further results in a compressive or massaging effect by the pad, as will be explained more fully hereinafter.

DETAILED DESCRIPTION OF THE INVENTION

Figure 1:
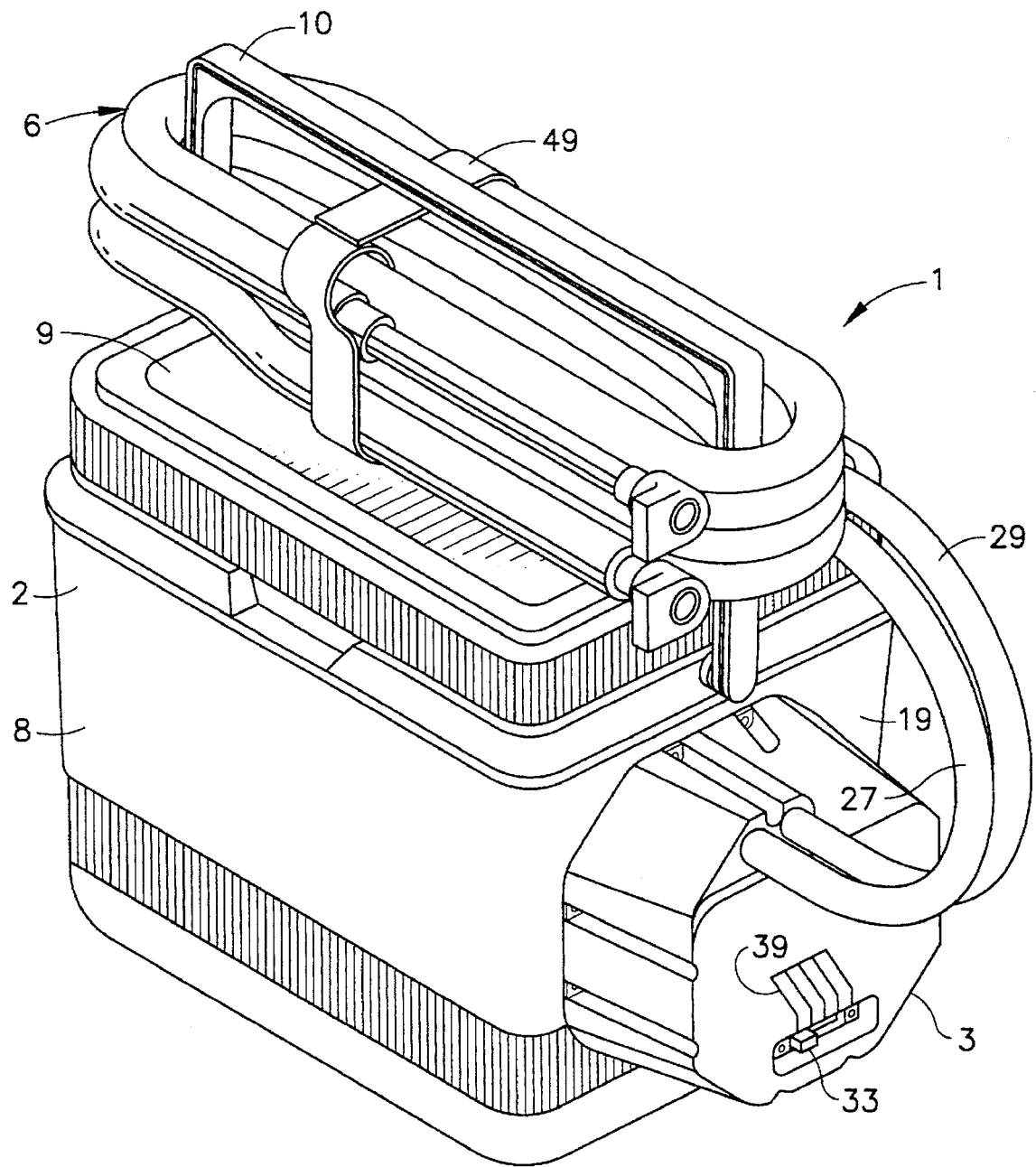
FIG. 1 is a perspective view illustrating the cooler, the pump housing, and the tube assembly of the cold therapy system of the present invention.
Figure 2:
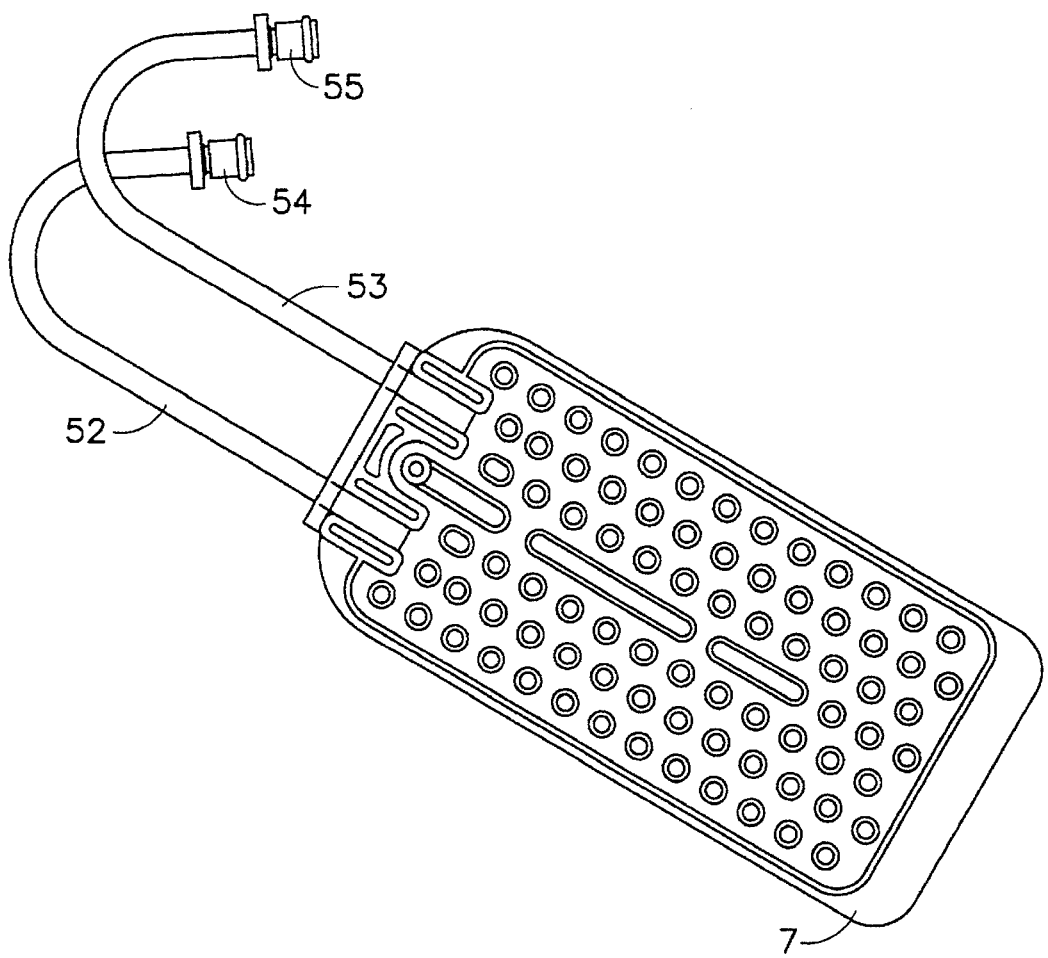
FIG. 2 is a plan view illustrating an exemplary pad for use with the cold therapy system of the present invention.

Throughout the Figures, like parts are given like index numerals. Reference is first made to FIGS. 1 and 2. In FIG. 1, the overall cold therapy system of the present invention is generally indicated at 1. The system comprises a portable cooler 2 which constitutes a reservoir for water and ice (not shown in FIG. 1). The cooler 2 has an exterior housing 3 affixed to one of its ends. The housing 3 contains a pump 4 and a pump control means 5 (see FIG. 4). The pump and reservoir are connected to a cooling pad 7 (shown in FIG. 2) by a delivery and return tube assembly, generally indicated at 6. As will be understood by one skilled in the art, the cooling pad may be placed against or wrapped about that part of the user requiring cold therapy.

Figure 3:
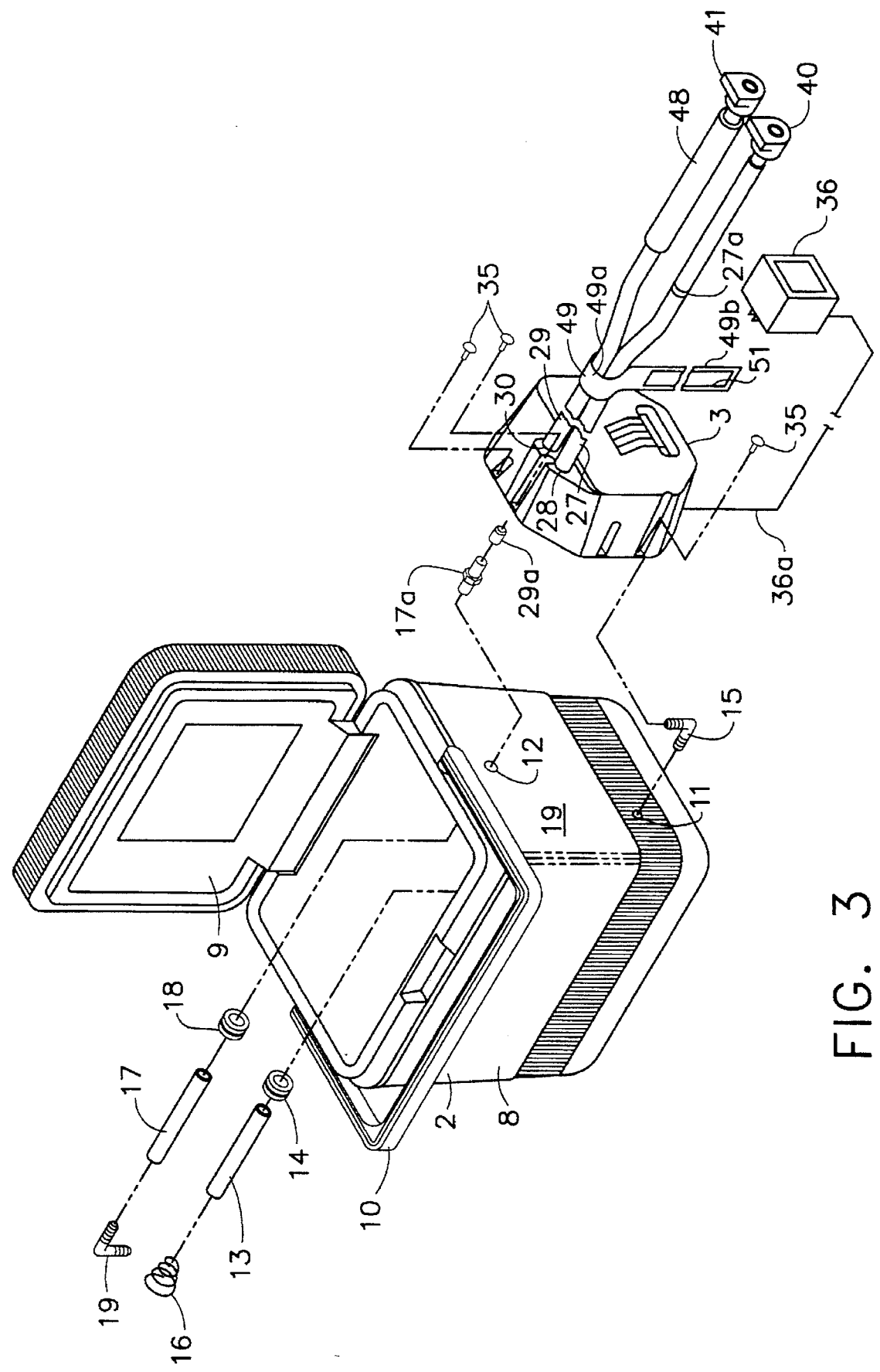
FIG. 3 is a fragmentary, exploded, perspective view of the cold therapy system of the present invention.

Each of the elements broadly set forth above, will now be described in detail. Referring to FIG. 3, the cooler 2 may be any appropriate conventional cooler having an insulative body 8 and an insulative lid 9. While it may be a separate element, the lid 9 is preferably hinged to the cooler body 8, and preferably makes a reasonably good sealing closure with the open top of body 8 so that the insulative qualities of the cooler are not compromised. The cooler 2 may have a bail-type handle 10, as is well known in the art. An example of a portable insulative cooler suitable for this purpose is manufactured by Gott Corporation of Winfield, Kans., under the model designation 1910.

An end wall 19 of the cooler body 8 is provided with a pair of bores 11 and 12 extending therethrough. A length of plastic tubing, such as PVC tubing is shown at 13 and extends through the bore 11. The bore 11 is provided with a resilient grommet 14 forming a seal between the inside surface of bore 11 and the exterior surface of tube 13. That part of tube 13 which extends exteriorly of cooler body 8 is provided with a conventional elbow connector 15. The structure just described comprises the outlet of reservoir body 8. The free end of tube 13, located within the reservoir body 8, is provided with a coiled spring-like strainer 16. Such strainers are well known in the art. The strainer 16 prevents ice chips or crystals from passing through the reservoir outlet.

A second tube 17, of plastic material such as PVC plastic, extends through bore 12 of the reservoir body end wall 19 and is similarly provided with a resilient sealing grommet 18 identical to previously described grommet 14. In this way, the tube 17 is sealed with respect to the bore 12. That end of tube 17 located within the reservoir body 8 is provided with a conventional elbow fitting 19, similar to fitting 15, and so placed as to direct fluid passing through tube 17 downwardly into the reservoir. It will be noted that the outlet bore 11 is located near the bottom of the reservoir body 8, while the inlet bore is located near the top of the reservoir body 8.

Figure 4:
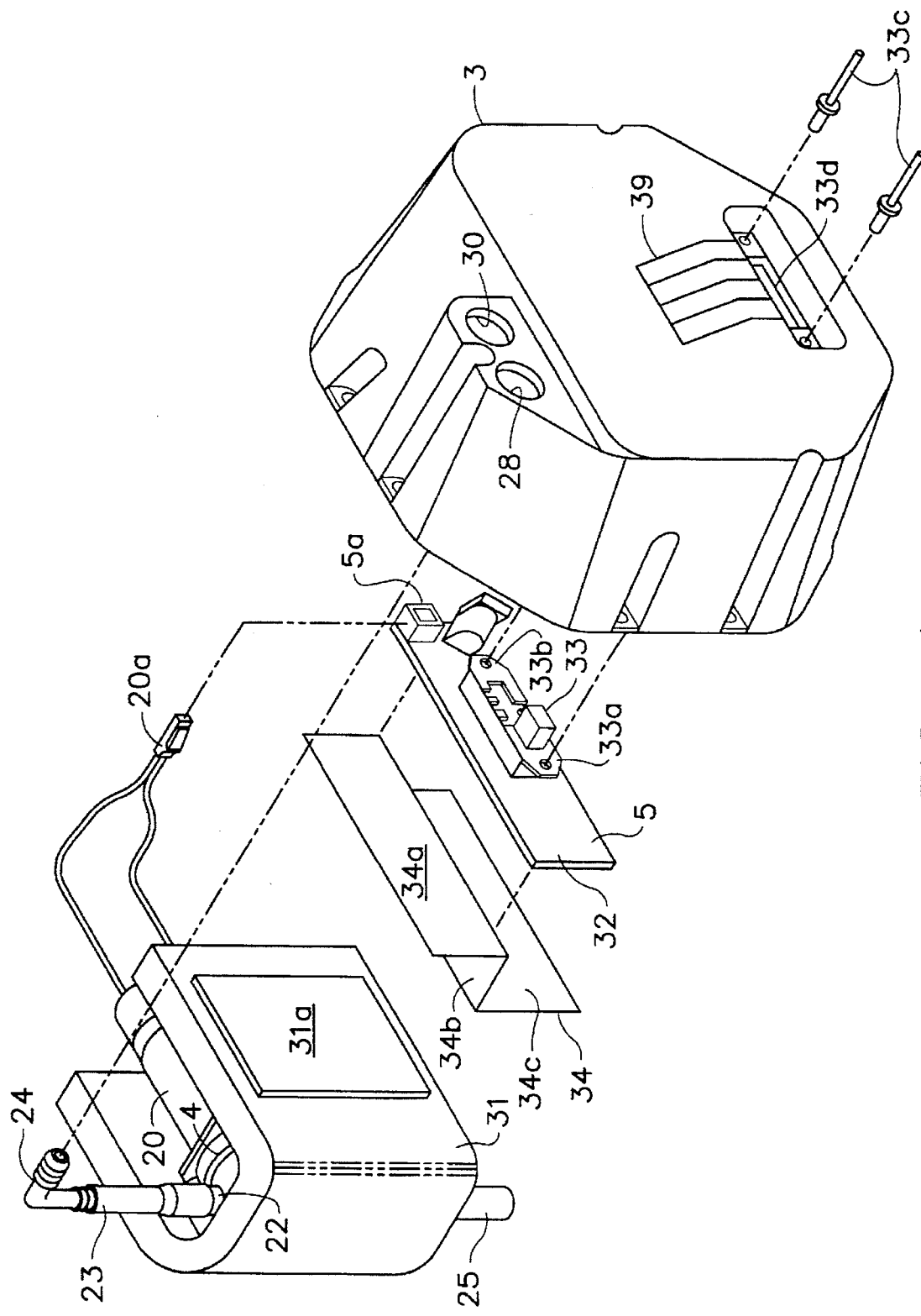
FIG. 4 is a fragmentary, exploded, perspective view illustrating the pump, the pump housing, and the control circuit board and switch of the present invention.

Reference is now made to FIGS. 3 and 4. The pump 4 includes, as a part thereof, a single-speed motor 20. The pump has a tubular inlet port (not shown) and a tubular outlet port 22. It will be understood that the inlet port is substantially identical to outlet port 22. Outlet port 22 is connected by means of a short piece of PVC tubing 23, or the like, to a connector elbow 24. The inlet of pump 4 is similarly connected by a short piece of PVC tubing 25, or the like, to the connector elbow 15 of the reservoir outlet. While not necessarily intended to be limiting, in an exemplary embodiment of the cold therapy system of the present system, all tubing used had an internal diameter of ¼ inch. In the particular embodiment, the pump 4 had tubular inlet and outlet members having an outside diameter of ⅜ inch. The PVC tube segments 23 and 25 may be stretched to enable connection between the ⅜ inch pump inlet and outlet elements and the ¼ inch elbow connectors 24 and 15. In an instance where the tubular pump inlet and outlet members and the elbow connectors 24 and 15 have the same outside diameter, standard ¼ inch internal diameter PVC tubing may be used throughout, without stretching.

The outlet elbow connector 24 of pump 4 is connected to a delivery tube 27. Delivery tube 27 passes through a perforation 28 in pump housing 3. The delivery tube 27 is provided with a check valve 27a, the purpose of which will be apparent hereinafter. A return tube 29 passes through a perforation 30 in pump housing 3. Return tube 29 is connected to reservoir inlet tube 17 by a conventional tube connector 17a. The end of return tube 29, near connector 17a is provided with an orifice 29a, or other appropriate restrictive means, to be further described hereinafter.

The pump 4 is preferably a single-speed, positive displacement pump, easy to prime. Excellent results have been achieved utilizing a 12 Volt DC pump manufactured by Shurflo, of Santa Anna, Calif. and having the Model No. 100-000-22. The pump 4 is capable of providing up to about 32 gallons per hour (32 gph) of liquid flow. However, when combined with the pulse-width modulating control circuit of the present invention, the pump-control circuit will provide selectable outputs to drive the pump at flow rates ranging from about 0.8 gallons per hour (0.8 gph) to about 4 gallons per hour (4 gph) without the usual difficulties encountered when running such a pump in a normal non-intermittent fashion which would require an extremely slow pump actuation rate to produce such low flow rates.

The pump 4 has wrapped thereabout a piece 31 of foamed material. The foamed material 31 serves several purposes. First of all, it separates the pump 4 from pump housing 3 and the adjacent end 19 of cooler body 8. As a consequence, the pump 4 is essentially free floating within pump housing 3 tending to reduce noise and vibration. Foamed material 31 also acts as an insulator for both heat and noise from the pump. The pump is supported within pump housing 3 by foamed material 31 and the connections to its inlet and outlet ports.

The pump control means 5 comprises a circuit board 32 including a four position manual switch 33. The pump control means 5 will be described in detail hereinafter. The switch portion 33 of the pump control means 5 is provided with lateral flanges 33a and 33b which are appropriately affixed to the inside front surface of pump housing 3 by blind rivets 33c or other appropriate fastening means. The pump housing 3 is provided with a transverse slot 33d through which the manual actuator of switch 33 extends.

A cover 34 of flexible, waterproof material is provided to protect the control means 5 from condensation or leakage from the pump. The cover 34 has a first segment 34a provided with a pressure sensitive adhesive so that it can be adhered to an inside surface of housing 3. The cover has a second segment 34b which overlies and extends rearwardly of the control means 5, when the control means is in its mounted position. Finally, the protective cover has a segment 34c which extends downwardly across the face of the printed circuit board of control means 5.

The insulative foam material 31, wrapped about pump 4, and its motor 20 is provided with a panel 31a of pressure sensitive adhesive material. This adhesive material 31a is adapted to be adhered to an inside surface of housing 3, when the switch 33, control means 5, protective cover 34 and the pump 4, motor 20 and foam wrap 31 are all positioned within housing 3. It will be noted from FIG. 4 that the motor 20 has a connector 20a adapted to be engaged in a connector 5a on the printed circuit board of pump control means 5. In this way, the output of the control means 5 is connected to the pump motor 20 to run the motor in any selected one of a number of intermittent modes, as will be set forth more fully hereinafter.

The pump housing is mounted on the end 19 of the cooler body 8 by a plurality of self-tapping screws some of which are shown at 35 in FIG. 3. The motor 20 of pump 4 constitutes a 12 Volt DC motor, as indicated above, and is connected to a source of power through the pump control means 5. The power source may be a battery, or it may be a 12-volt power supply, as shown at 36 in FIG. 3. Power supply 36 may be connected to any conventional household outlet, or the like. Power supply 36 has an electrical cord 36a extending therefrom. The free end of cord 36a is provided with a jack (not shown) receivable within a socket (not shown) in the bottom surface of pump housing 3. The socket is appropriately connected to the pump control means 5.

It is within the scope of the invention to provide indicia on the front face of the pump housing to indicate the position of the manual actuator of switch 33. Such indicia is suggested at 39 in FIGS. 1 and 4. The indicia may be color coded and may be provided with legends reading from left to right in FIGS. 1 and 4 as follows: "STOP", "HIGH", "MEDIUM", and "LOW". Alternatively, they may read from left to right as follows: "STOP", "COLDEST", "COLD", and "COOL".

Figure 5:
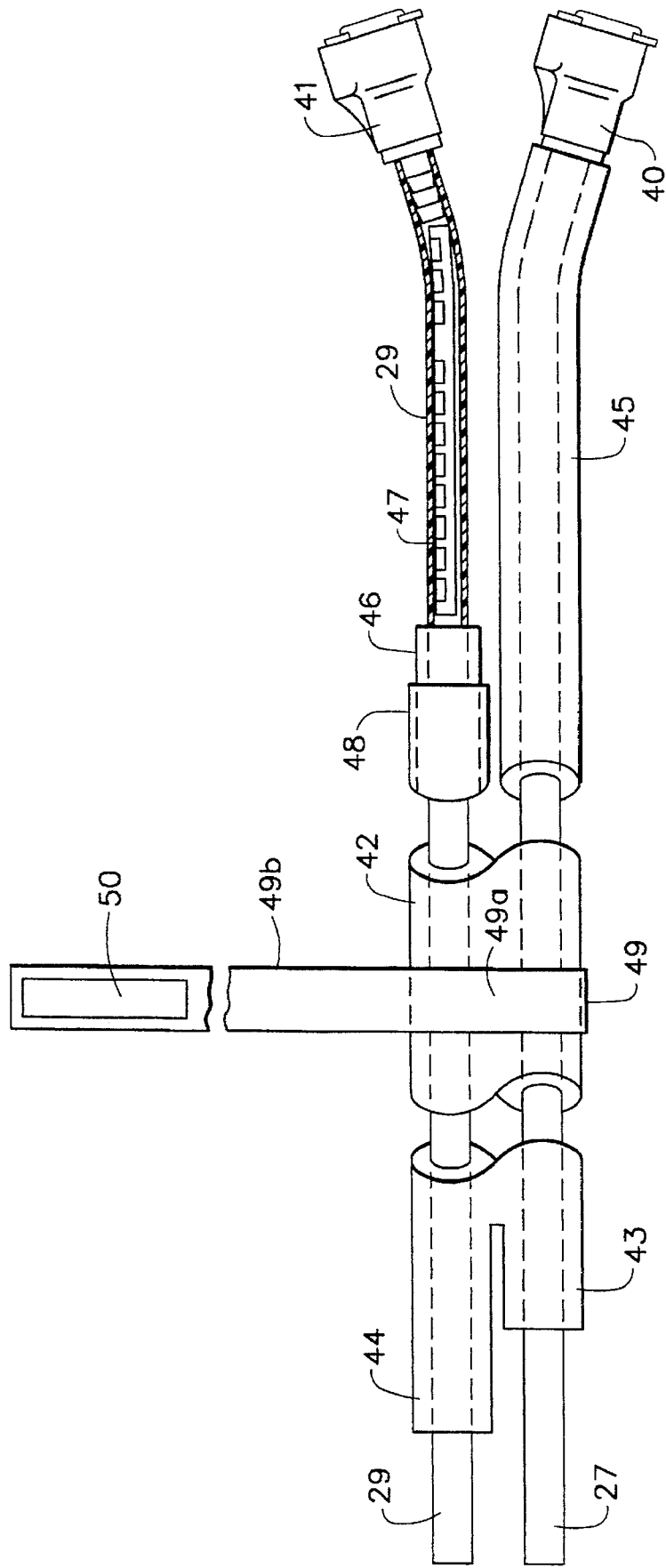
FIG. 5 is a fragmentary elevational view of the tube assembly of the present invention.

As indicated above, the outlet elbow 24 of pump 4 is connected to a delivery tube 27 which extends through perforation 28 in pump housing 3. A return tube 29 extends through a perforation 30 in the pump housing 3 and is connected to the inlet tube 17 of reservoir body 8 by connector 17a. Delivery and return tubes 27 and 29 constitute the tube assembly 6, and are best shown in FIG. 5.

In an exemplary embodiment, the delivery and return tubes 27 and 29 comprised PVC tubing having a ¼ inch internal diameter. At their free ends, delivery and return tubes 27 and 29 are provided respectively with female quick disconnect tube couplings 40 and 41, respectively. The female couplings 40 and 41 are in-line couplings preferably of the type having shut-off means. Preferably, they are provided with shrouded release buttons to prevent accidental disconnects. Female couplings of this type are available, for example, from Colder Products Company of St. Paul, Minn., having a part number PLCD 170-04.

The delivery and return tubes 27 and 29 are provided substantially throughout their length with a foam tube insulation covering 42. The foam tube insulation 42 comprises two tubular members having an inside diameter to just nicely receive the delivery and return tubes 27 and 29 and which are joined together by a web located therebetween, so that the foam tube insulation comprises an integral, one-piece structure accommodating both the delivery and return tubes 27 and 29. Near its rearward end the foam tube insulation 42 is split into two separate end portions 43 and 44 so that they can enter perforations 28 and 30 of pump housing 3. This is shown in FIGS. 1 and 3. The foam tube insulation end portion 43 surrounding delivery tube 27 extends substantially to the joinder of delivery tube 27 to output elbow 24 of pump 4. The foam tube insulation end portion 44 surrounding return tube 29 extends substantially to the point where return tube 29 is engaged by connector 17a.

At its forward end, the foam tube insulation 42 is again split into two separate end portions 45 and 46. End portion 45, surrounding delivery tube 27, extends to the female coupling 40. End 46, on the other hand, terminates short of female coupling 41, exposing a length of return tube 29. The exposed portion of return tube 29 contains a liquid crystal temperature indicator shown at 47, or other appropriate temperature indicator. Temperature indicator 47 monitors and displays the temperature of the water returning from pad 7 to reservoir 8. Liquid crystal in-line temperature indicators are available, for example, from Hallcrest of Glenview, Ill. The liquid temperature indicator 47 is held in place within return tube 29 by frictional engagement between temperature indicator 47 and the inside surface of return tube 29.

The forward end portions 45 and 46 of the foam tube insulation 42 are separated from each other for a distance sufficient to accommodate an additional length of foam tubing insulation 48. Insulative member 48 has an internal diameter of such size as to be slidable on foam tube insulation end portion 46 between a retracted position wherein it completely exposes temperature indicator 47 (as shown in FIG. 5), and a position wherein the forward end of insulative member 48 contacts female coupling 41, while the rearward end of insulative member 48 slightly overlaps the forwardmost end of foam tube insulation end portion 46. Thus, the insulative member 48 may be used to cover that portion of return tube 29 containing temperature indicator 47 between readings thereof. As will be understood by one skilled in the art, the temperature indicator 47 and its slidable insulative member 48 could have been provided in association with delivery tube 27, if desired.

The tubing assembly 6 is completed by a storage strap 49. Storage strap 49 has a portion 49a which extends about tube assembly 6. Storage strap 49 has a laterally extending portion 49b. One side of storage strap portion 49b has affixed thereto one part of a hook and loop tape assembly, as indicated at 50 in FIG. 5. The other side of the portion 49b of storage strap 49 has affixed thereto the other part of the hook and loop assembly, as indicated at 51 in FIG. 4. The storage strap 49 enables the tube assembly 6 to be coiled and maintained in a coiled position. Preferably, the tube assembly 6 is coiled about the cooler handle 10 and is maintained in this position by storage strap 49, as shown in FIG. 1.

The cold therapy system of the present invention is provided with cooling pad 7 (see FIG. 2). Cooling pad 7 is conventional and may be of any appropriate size or shape. The cooling pad 7 is normally made up of a pair of compliant plastic plies joined together so as to form a tortuous path for the chilled water entering and leaving the pad. For this purpose, the pad is provided with a delivery tube 52 and a return tube 53. The delivery and return tubes 52 and 53 may comprise ¼ inch PVC tubing. One end of each of delivery and return tubes 52 and 53 is attached to cooling pad 7. The other end of each of delivery and return tubes 52 and 53 are provided with straight through male couplings adapted to cooperate with female couplings 40 and 41 (see FIG. 5). Such straight through male couplers are available, for example, from Colder Products Company of St. Paul, Minn., having a part number LC 220-04. It would be within the scope of the invention to use male couplers with shut-off means. It would also be within the scope of the invention to provide each of delivery and return tubes 52 and 53 with foam tube insulation, in substantially the same manner described with respect to the foam tube insulation 42 of FIG. 5.

Figure 8:
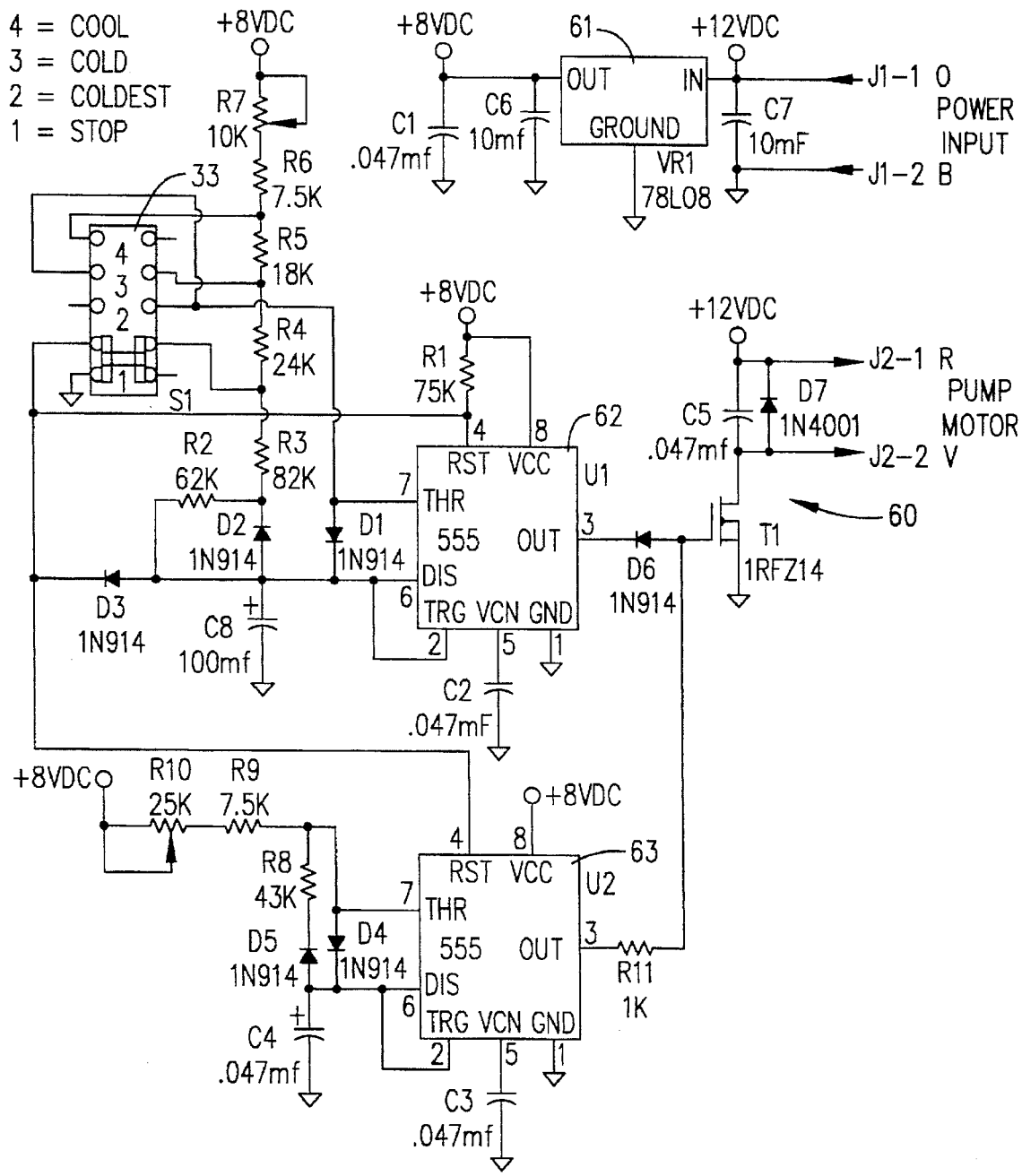
FIG. 8 is a schematic diagram of the electronics that drive the pump motor of the present invention.

FIG. 8 is a schematic diagram of the electronics of the present invention (generally designated by the index numeral 60) which are mounted on the printed circuit board of pump control means 5, and which are used to drive the pump motor 20. The power input is a 12 Volt DC power supply provided by the adapter 36. This 12 Volt DC power supply is fed into a voltage regulator 61, which has a regulated output voltage of +8 Volts DC, which is used throughout the circuit of the electronics 60.

The electronics 60 include two timer chips designated by the index numerals 62 and 63. Timer chips 62 and 63 are each identical "555"-timers, which are used in the conventional sense to form astable multivibrators. The duty cycle of timer chip 62 is variable, thereby making that portion of the timer circuitry into a pulse-width modulating circuit. This duty cycle is manually controlled by use of the previously mentioned four-position selector switch.

Selector switch 33 can be used to stop the output pulses from timer 62 when its "STOP" position, (position 1 in FIG. 8) is selected. In this mode of operation, the "Reset" inputs of both timer chips 62 and 63 are set to DC Common, which essentially is 0 volts.

When selector switch 33 is in any of its operating positions (i.e., in a position other than the "1" STOP position), timer 63 will output a continuous pulse train at approximately 2 kHz, and the duty cycle of each period of this 2 kHz pulse train will be approximately 25%. On FIG. 9, the waveform of this pulse train with respect to the time domain of the output pulses from timer 62 is a very dense set of constant pulses, depicted by the waveform timing diagram 64, in which the pulses are so close to one another that they really cannot be drawn accurately on a chart at this scale. Using an expanded time scale, the pulse train can be more readily discerned from the timing diagram 65 which shows a 25% duty cycle pulse train, in which the period of each pulse is about 0.5 msec. The ON-time is about 0.125 msec., and the OFF-time is about 0.375 msec.

If this pulse train signal were directly controlling the output transistor T1 (irrespective of the output signal from timer chip 62), the pump motor 20 would run at about 25% of its full speed due to the 25% duty cycle of the pulse train. The pump itself would, therefore, run at about 8 GPH. Timer chip 63 has its output connected through resistor R11 to the output transistor T1. The output of timer 62 is also connected to output transistor T1 through a diode D6. When the output signal from timer 62 is introduced in this configuration, output transistor T1 operates as the output stage of an AND-gate, in which the outputs of the two timers 62 and 63 are the inputs. In other words, output transistor T1 will be turned ON only when both outputs from timers 62 and 63 are in their logic 1 or ON-state. When transistor T1 is turned ON, it will allow electricity to be conducted through pump motor 20, thereby causing that pump motor to rotate. If output transistor T1 were turned on 100% of the time, pump motor 20 of the illustrated embodiment would cause the pump 4 to run at a flow rate of approximately 32 gallons per hour (GPH). This does not occur because the duty cycle of timer 62 is fixed at one of the values of 50%, 25% or 11% as described hereinbelow, and the duty cycle of timer 63 is fixed at 25%, so their overall combined duty cycles are much less than 100%.

Figure 9:
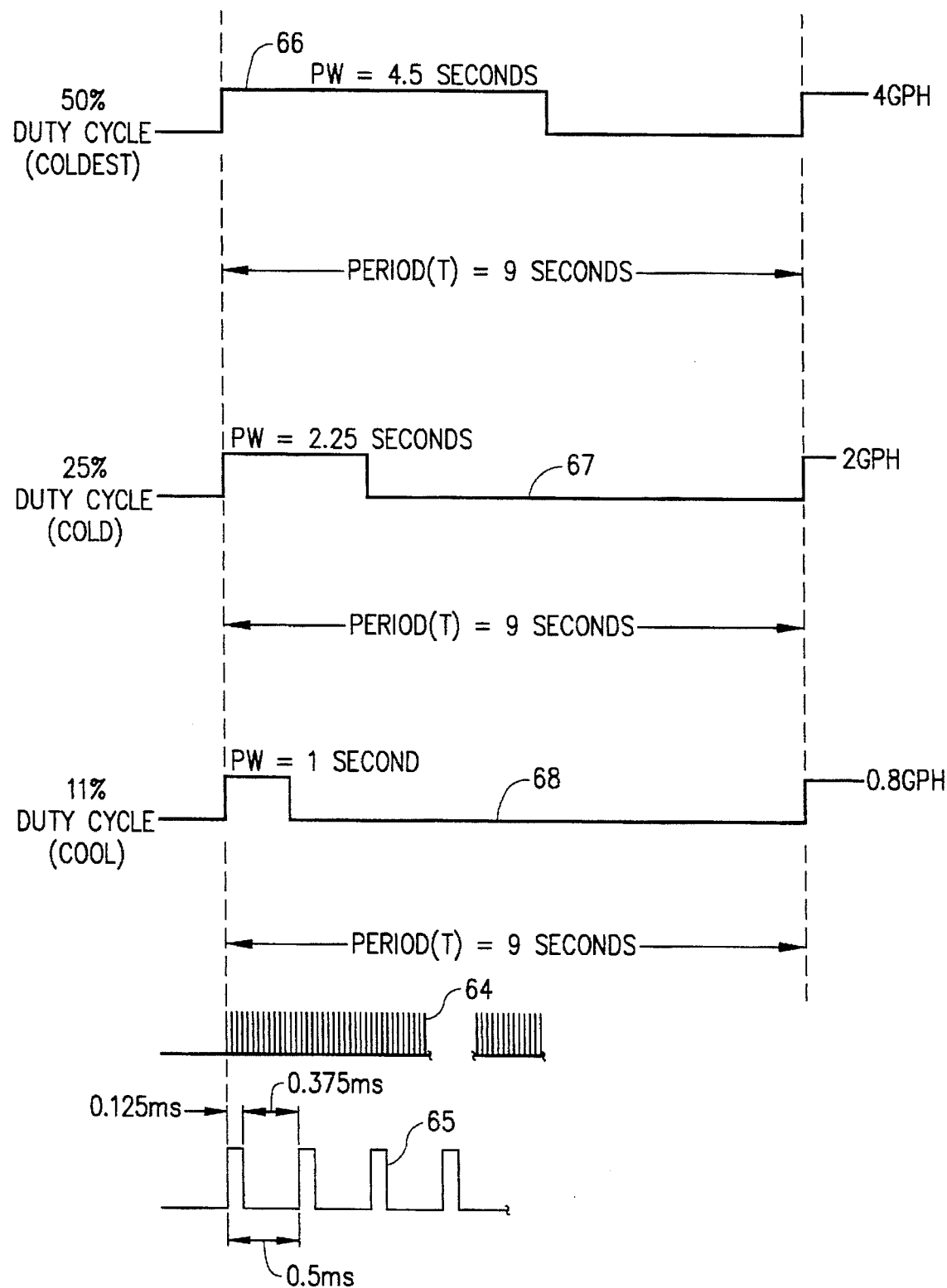
FIG. 9 is a timing diagram depicting the output pulses of the timer circuits shown at FIG. 8.

When the selector switch 33 is moved to position "2", pump motor 20 is caused to run for the longest duration per period of time, thereby providing the "COLDEST" performance condition. In this mode of operation, timer 62 is caused to run at approximately a 50% duty cycle, having a period of about 9 seconds. The waveform of the output of timer 62 in this mode is shown on FIG. 9 as timing diagram 66. As can be seen in FIG. 9, the ON-time is about 4.5 seconds, and the OFF-time is also about 4.5 seconds.

When selector switch 33 is placed in its position No. "3", pump motor 20 is caused to operate in its intermediate "COLDER" operating mode, which means the motor will run for a somewhat shorter duration per period of time because the duty cycle of timer 62 now becomes about 25%. As can be seen in FIG. 9, the waveform of the output of timer 62 in this mode is depicted by the timing diagram 67, having an ON-time of about 2.25 seconds, and an OFF-time of 6.75 seconds. The variation in the output duty cycle of timer 62 is due to the fact that selector switch 33 provides a different resistance ratio among the array of resistors R7, R6, R5, R4, R3, and P,2 in FIG. 8. As can be seen in FIG. 8, in the "COLDEST" mode of operation, the threshold input (pin 7) of timer 62 is connected to the node between R4 and R3. In the "COLDER" mode, this threshold input of timer 62 is connected to the node between resistors R4 and R5.

In the "COLD" mode, the output duty cycle of timer 62 is about 11%, and this waveform is depicted in FIG. 9 by the timing diagram 68. In this operating mode, the output of timer 62 is ON for about one second, and then OFF for about eight seconds. In this "COLD" mode of operation, the threshold input of timer 64 is connected to the node between resistors R5 and R6.

Since the output of timer 63 is a 25% duty cycle waveform, the effective duty cycle controlling output transistor T1 is about one-fourth the duty cycle of timer 62. When selector switch 33 is in its position "2" "COLDEST" position, the duty cycle of timer 62 is about 50%. When combined with the 25% duty cycle of timer 63, the effective output transistor T1 duty cycle is approximately 12.5% (0.50×0.25). In this mode, pump motor 20 will pump at about one-eighth of its maximum capacity, or about 4 GPH. When selector switch 33 is in its "3" "COLDER" position, pump motor 20 will operate at an effective duty cycle of about 6.25% (¼×¼) which will cause the pump to operate at a rate of about 2 GPH. When selector switch 33 is in its position "4" COLD position, pump motor 20 will be caused to operate at an effective duty cycle of about 2.77% (1/9×1/4) thereby driving the pump at about 0.8 GPH. It will be understood that motor 20 always runs at a constant speed during those time intervals that an output pulse from timer 62 is at its logic 1 ON-state. The primary effect of the electronic signal switched by output transistor T1 is to further reduce the pumping capacity of the cold therapy system without attempting to force motor 20 to rotate more slowly (which would increase the motor's cost significantly).

The remaining timing circuitry associated with timers 62 and 63 is relatively standard circuitry known in the art. It will be understood that many other types of timing schemes could be implemented to provide the pulse-width modulating operation that drives output transistor T1, including the relatively high-frequency pulse train aspect of its operating waveform provided by timer 63 in the illustrated embodiment.

Figure 6:
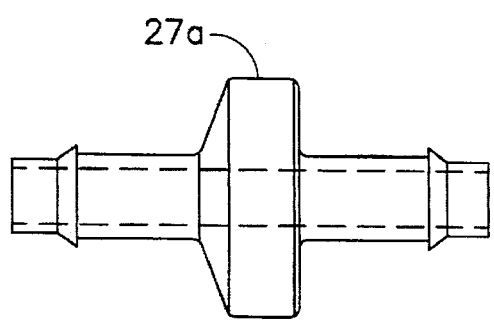
FIG. 6 is an elevational view of an exemplary check valve used in the output line of the present invention.

As mentioned heretofore, and as shown in FIGS. 3 and 6, the output line 27 is provided with a check valve 27a. The check valve is of known construction and is readily available. The check valve has an internal seat and a diaphragm which is lifted from the seat when fluid flow is in the desired direction and which seals against the seat when fluid attempts to flow in the opposite direction. The check valve assures that fluid from pad 7 will not flow back to the pump 4 during those times of the intermittent running of the pump motor when transistor T1 is not in its logic "1" or ON-state when there is no output from timer 62.

Figure 7:
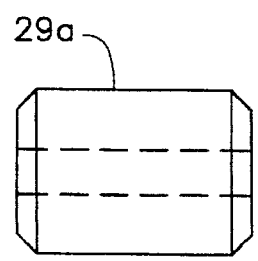
FIG. 7 is an elevational view of an exemplary orifice inserted in the return line of the present invention.

The orifice 29a, previously mentioned and illustrated in FIGS. 3 and 7 is provided in return line 29. The purpose of orifice 29a is to control the descent of pressure in pad 7 during motor-off times when there is no signal from timer 62 to transistor T1. In the exemplary embodiment described, an orifice of 0.06 inch was found adequate when the various connections and the output and return tubes 27 and 29 had an internal diameter of 1/4 inch. It would be within the scope of the invention to replace orifice 29a with any appropriate restriction. For example, some or all of the return line 29 could comprise tubing of lesser diameter.

It has been found that the pad not only serves as a temperature transferring device, but also has an intermittent compressive or massaging effect on that part of the user against which it is located or about which it is wrapped. This is due to a number of factors: the intermittent operation of the pump; the downstream restriction means; and the fact that the pad is compliant. The compressive effect adds to the therapeutic value of the system.

To obtain the benefit of the intermittent compression imparted by the pad, the pad itself must be of such nature that it can be wrapped securely about that part of the user being treated. Alternatively the pad must be securely located on the treatment site by an overwrap. In yet another instance the pad may be located between the treatment site and a relatively firm surface (i.e. between the treatment site and a mattress, or the like). The firmness with which the pad is held against the treatment site will determine the degree of intermittent compression imparted by the pad. The compressive effect will also be somewhat greater at the "coldest" setting than at the "cool" setting.

The cold therapy system of the present invention having been described in detail, its manner of operation may now be set forth. Reference is made to FIG. 1. As a first step, the user releases storage strap 49 and uncoils tubing assembly 6. The female and male couplings 40 and 54 of delivery tubes 27 and 52 are joined together. In a similar fashion, the female coupling 41 and male coupling 55 of return tubes 29 and 53 are also joined together so that the pad 7 is properly connected to the system.

With the tube assembly 6 removed from cooler 2, the cooler handle 10 can be lowered as shown in FIG. 3 and the cooler lid 9 can be pivoted to its open position. At this stage, the reservoir 8 is filled with water and ice. The lid 9 of reservoir body 8 is thereafter closed. Care must be taken to introduce enough water that outlet tube 13, connected to the inlet of pump 4, is submerged during operation.

Since pump 4 is mounted within pump housing 3, externally of cooler 2, heat generated by the pump will be outside the cooler. Pump 4 is mounted in a floating fashion within pump housing 3 and is surrounded by the foamed material 31. It will be remembered that the foam material 31 serves as an insulator against both noise and heat generated by the pump. Since the pump is mounted within pump housing 3, externally of cooler 2, there is no set up or necessary tube connection with respect to the pump. External positioning of the pump also assures that the lid 9 of cooler 2 may be fully closed during operation. Having filled the reservoir body 8 with water and ice, the user can close the cooler lid 9 and connect the power supply jack (not shown) to the socket (not shown) in pump housing 3. The power supply 36 can thereafter be plugged into an ordinary wall socket and the pump can be started by shifting the manual element of switch 33 from its "STOP" position to any desired one of its three "ON" positions.

To complete the operation, the pad 7 is placed against or wrapped about that body part to be treated, and the cold therapy treatment is continued for the desired length of time. At the end of the cold therapy treatment, the pump is deactivated by locating switch 34 in its "STOP" position. The power pack 36 is disconnected from the wall outlet and the power pack jack is removed from the pump housing socket. The pad 7 is disconnected from tube assembly 6 at the male and female couplings 40/54 and 41/55. Little or no leakage will occur at these couplings 40 and 41 if they each have an internal shut-off mechanism. The cooler lid 9 is opened and the reservoir body 8 is emptied of ice and water. Cooler lid 9 is then pivoted to its closed position and the cooler handle is shifted to its upright position, as shown in FIG. 1. Thereafter, the hose assembly 6 is coiled about the cooler handle 10 in the manner shown in FIG. 1, and is maintained in position by storage strap 49.

In some instances it may be desirable to support the cold therapy system of the present invention on a bed frame or the like. This can be accomplished by providing a support bracket of the type, for example, taught in the above-noted U.S. Pat. No. 5,476,489.

From the above description, it will be apparent to one skilled in the art that the present invention provides a portable cold therapy system characterized by more precise and repeatable temperature control, better pump efficiency and performance, and a therapeutic intermittent compressive effect at the treatment site.

Modifications may be made in the invention without departing from the spirit of it. For example, it would be within the scope of the invention to provide timer 62 with more than three modes of operation. However, a three mode system has been found to be sufficient for most purposes.

What is claimed:

1. A control system for the electric motor of a fluid pump, said control system comprising an electric DC motor, a source of DC current, a first astable multivibrator having a continuous first output signal at a fixed duty cycle, a second astable multivibrator operating at a frequency lower than said first astable multivibrator and at a fixed period and having a second output signal at a selectable duty cycle, an output transistor having an input in communication with each of said first and second output signals, said output transistor providing a third output signal to drive said motor when both said first and second output signals are simultaneously in a state to turn on said transistor, said fixed duty cycle determining the speed at which said motor runs and said selectable duty cycle determining the amount of time said motor runs per period of said selectable duty cycle.

2. The control system claimed in claim 1 further comprising means to select at least one predetermined duty cycle from said variable duty cycle.

3. The control system claimed in claim 2 wherein said selecting means comprises a manual selector switch having a position for each predetermined duty cycle to be selected.

4. A control system for determining the flow rate of water in a water-circulating cold therapy device of the type comprising a reservoir containing ice and water, a pump and an electric DC drive motor therefor, a pump inlet connected to said reservoir, a waterproof cold therapy application pad having an inlet and an outlet and a path for water therein connecting said pad inlet and outlet, a pump outlet, an insulated delivery tube connecting said pump outlet and said pad inlet, an inlet port in said reservoir, and an insulated return tube connecting said pad outlet and said reservoir inlet, said control system comprising a source of DC current for said pump motor, a first astable multivibrator having a continuous first output signal at a fixed duty cycle, a second astable multivibrator operating at a frequency lower than said first multivibrator and at a fixed period and having a second output signal at a selectable duty cycle, an output transistor having an input in communication with each of said first and second output signals, said output transistor providing a third output signal to drive said motor when both said first and second output signals are simultaneously in a state to turn on said transistor, said fixed duty cycle determining the speed at which said motor runs and said selectable duty cycle determining the amount of time said motor runs per period of said selectable duty cycle.

5. The control system claimed in claim 4 further comprising means to select at least one predetermined duty cycle from said variable duty cycle.

6. The control system claimed in claim 4 wherein said selecting means comprises a manual selector switch having a position for each predetermined duty cycle to be selected.

7. The control system claimed in claim 6 including three selectable predetermined duty cycles comprising a 50% duty cycle, a 25% duty cycle and an 11% duty cycle, said 50%, 25% and 11% duty cycles corresponding, respectively, to COLDEST, COLD and COOL modes of operation of said cold therapy system.

8. The control system claimed in claim 7 wherein said fixed duty cycle comprises a 25% duty cycle.

9. The control system claimed in claim 4 wherein said cold therapy application pad is applied to a treatment site of a patient and means to maintain said pad firmly against said site, whereby to cause said pad to impart intermittent compression to said site as a result of said variable duty cycle.

10. The control system claimed in claim 4 including a check valve in said delivery tube permitting flow only from said pump to said pad, whereby to prevent the flow of water from said pad to said pump when said pump motor is not running.

11. The control system claimed in claim 4 including an orifice in said return line whereby to control the descent of water in said pad during motor-off times.

12. A method of controlling the flow rate of water in a water-circulating cold therapy device of the type comprising a reservoir containing ice and water, a pump and a DC electric drive motor therefor, a pump inlet connected to said reservoir, a waterproof cold therapy application pad having an inlet and an outlet and a path for water therein connecting said pad inlet and outlet, a pump outlet, an insulated delivery tube connecting said pump outlet and said pad inlet, an inlet port in said reservoir, an insulated return tube connecting said pad outlet and said reservoir inlet, and a source of DC current for said pump, said control method comprising the steps of connecting said source of current to a first astable multivibrator providing a continuous first output signal at a fixed duty cycle, connecting said source of current to a second astable multivibrator operating at a frequency lower than said first astable multivibrator and at a fixed period and providing a second output signal at a selectable duty cycle, providing an output transistor having an input in connection with each of said first and second signals, said transistor providing a third output signal when both said first and second output signals are simultaneously in a state to turn on said transistor, using said third output signal to drive said pump motor at a speed less than its maximum speed using said fixed duty cycle to determine said pump motor speed and using said selectable duty cycle to determine the amount of time said pump motor runs per period of said selectable duty cycle.

13. The method claimed in claim 12 including the step of providing a number of predetermined selectable duty cycles within said variable duty cycle, providing a manual selector switch, and providing a position on said switch for each of said selectable duty cycles.

14. The method claimed in claim 13 wherein said selectable duty cycles comprise a 50% duty cycle, a 25% duty cycle and an 11% duty cycle which correspond, respectively, to COLDEST, COLD and COOL modes of operation of said cold therapy device.

15. The method claimed in claim 14 wherein said first continuous duty cycle is a 25% duty cycle.

16. The method claimed in claim 12 wherein said pad expands and contracts by virtue of said variable duty cycle and including the step of applying said pad to the treatment site of a patient in such a way as to cause said expansion and contraction of said pad to impart intermittent compression to said treatment site.

17. The method claimed in claim 12 including the step of providing a check valve in said delivery tube permitting water to flow in said delivery tube from said pump outlet to said pad inlet.

18. The method claimed in claim 12 including the step of controlling the descent of water pressure in said pad during motor-off times by providing an orifice in said return line.

* * * * *